(12) United States Patent
Edwards

(10) Patent No.: US 7,163,689 B2
(45) Date of Patent: *Jan. 16, 2007

(54) INTRAVENOUS VALPROATE FOR ACUTE TREATMENT OF MIGRAINE HEADACHE

(76) Inventor: Keith R. Edwards, c/o Neurological Consultants, P.C. Medical Office Building, 140 Hospital Dr., Bennington, VT (US) 05201

( * ) Notice: Subject to any disclaimer, the term of this patent is extended or adjusted under 35 U.S.C. 154(b) by 0 days.

This patent is subject to a terminal disclaimer.

(21) Appl. No.: 11/173,922

(22) Filed: Jul. 1, 2005

(65) Prior Publication Data

US 2005/0245611 A1    Nov. 3, 2005

Related U.S. Application Data

(63) Continuation of application No. 10/034,981, filed on Dec. 27, 2001, which is a continuation of application No. 09/564,521, filed on May 4, 2000, now abandoned.

(60) Provisional application No. 60/132,416, filed on May 4, 1999.

(51) Int. Cl.
*A61K 13/00* (2006.01)
*A61K 9/00* (2006.01)
*A61K 31/19* (2006.01)

(52) U.S. Cl. .................. 424/422; 424/400; 514/557

(58) Field of Classification Search ............... 424/422, 424/400; 514/763, 557
See application file for complete search history.

(56) References Cited

U.S. PATENT DOCUMENTS

| 5,102,913 A | | 4/1992 | Halikas | |
|---|---|---|---|---|
| 5,432,176 A | * | 7/1995 | Walser | 514/254.07 |
| 5,767,117 A | | 6/1998 | Moskowitz | |

FOREIGN PATENT DOCUMENTS

| WO | WO-99/66920 A1 | 12/1999 |
|---|---|---|
| WO | WO-00/66109 A1 | 11/2000 |

OTHER PUBLICATIONS

Welch, "Drug Therapy: Drug Therapy Migraiine," The New England Journal of Medicine, Nov. 11, 1993, pp. 1476-1483.*
Arnold, G., et al., "Valproic acid in the prophylactic treatment of migraine," *Nervenarzt*, vol. 69(10):913-918 (1998).
Curtrer, F.M., et al., "Possible mechanisms of valproate in migraine prophylaxis," *Cephalagia*, vol. 17:93-100 (1997).
Edwards, Keith R., et al., "Sodium valproate for the treatment of chronic daily headaches," *Cephalagia*, vol. 19:453 (1999), Abstract No. VI-G5-1.
Edwards, Keith R., et al., "Acute Treatment of Migraine Headeach with Intravenous Valproate (Depecon)," *Epilepsia*, vol. 40(Suppl. 7):143 (1999), Abstract No. 2,240.
Edwards, Keith R, et al., "Intravenous valproate for abortive treatment of acute migraine headache. Is there an anti-convulsant mechanism?" *Epilepsia*, vol. 40(Suppl. 2):36 (1999).
Edwards, Keith R, "Intravenous valproate for acute treatment of migraine headache," *Cephalalgia*, vol. 19:356 (1999), Abstract No. II-GI-7.
Hering, R., et al., "Sodium valproate in the prophylactic treatment of migraine: a double-blind study versus placebo," *Cephalalgia*, vol. 12:81-84 (1992).
Jensen, R., et al., "Sodium valproate has a prophylactic effect in migraine worhour aura: a triple-blind, placebo-controlled crossover study," *Neurology*, vol. 44:647-651 (1994).
Mathew, Ninan T., et al., "Repetitive intravenous administration of valproate sodium in intractable migraine: Comparison with intravenous Dihydroegotamine (DHE)." *Neurology*, vol. 54(Suppl. 3):A22 (2000).
Mathew, Ninan T., et al., "Migraine prophylaxis with divalproex," *Arch Neurol*, vol. 17:281-286 (1995).
Ramsay, R.E., et al., "The tolerability and safty of valproate sodium injectino given as an intravenous infusion," *Journal of Epilepsy*, vol. 10(4):187-193 (1997).
Tran, Bihn N., et al., "Can valproate prevent migraine headache?" *Journal of Pharmacy Technology*, vol. 13(4):163-168 (1997).
"Intravenous valproate sodium for intractible mitraine," *Journal of Pharmacy Technology*, vol. 16(4):161 (2000).
Edwards, Keith R., et al., "Intravenous Valproate For Acute Treatment Of Migraine Headache," *Headache*, vol. 39(5):201 (1999), Poster #76.
Kailasam, J., et al., "Intravenous Valproate Sodium (Depacon) Aborts Migraine Rapidly: A Preliminary Report," *Headache*, vol. 39(5):168-169 (1999).
Depacon™: Valproate Sodium Injection, Abbott Laboratories 06-9798-R2, Jan. 1998; (No. 1564).

* cited by examiner

*Primary Examiner*—Blessing Fubara
(74) *Attorney, Agent, or Firm*—Lahive & Cockfield, LLP; Giulio A. DeConti, Jr., Esq.; Debra J. Milasincic, Esq.

(57) ABSTRACT

The present invention features a novel therapy for effecting acute treatment of migraine headache. The therapy involves intravenous administration of valproate and is equal to and in some respects superior to previously-known therapies for abortive treatment of prolonged moderate to severe acute migraine headache.

9 Claims, No Drawings

INTRAVENOUS VALPROATE FOR ACUTE TREATMENT OF MIGRAINE HEADACHE

RELATED APPLICATIONS

This application is a continuation of U.S. application Ser. No. 10/034,981, filed Dec. 27, 2001, entitled "Intravenous Valproate for Acute Treatment of Migraine Headache", which is a continuation of U.S. application Ser. No. 09/564,521, filed May 4, 2000 now abandoned, which claims the benefit of prior-filed U.S. Provisional Patent Application Ser. No. 60/132,416, filed May 4, 1999. The content of the referenced applications are incorporated herein by reference.

BACKGROUND OF THE INVENTION

Migraine headache is a chronic and disabling condition affecting a significant portion of the population throughout the world. The pharmacologic management of migraine has traditionally focused on two approaches: symptomatic or acute treatment and prophylactic therapy. The objective of acute treatment is to reduce the intensity and duration of pain with its attendant symptoms and to optimize the patient's ability to function normally whereas the major objective of prophylactic therapy is the reduction of frequency, duration, and intensity of attacks.

A variety of treatment strategies are available for the prophylactic treatment of migraines including beta-blocking drugs (e.g., propranolol), amitriptyline, flunarizine, serotonin antagonists (e.g., methysergide) and nonsteroidal anti-inflammatory drugs (e.g., naproxen) are the major classes of agents that have been used in the prophylactic treatment of migraines. See e.g., Deleu et al (1998) *Clin. Neuropharmacol.* 21:267–79 for review. Strategies for the acute treatment of migraines are also known which generally involve the use of simple analgesics, nonsteroidal anti-inflammatory drugs, antiemetics, narcotic analgesics, ergot derivatives, or serotonin-agonists, either alone or in combination. For example, dihydroergotamine (DHE) has been used for several decades for treatment of acute migraine headache and produces good relief in 70–80% of subjects at 2 hours after administration (Callaham and Raskin (1986) *Headache* 26;168–171). Sumatriptan produces similar efficacy, as do several newer serotonin 1B/1D receptor agonists (Cady et al. (1991) *JAMA* 265:2831–2835; Mathew et al. (1992) *Arch Neurol.* 49:1271–1276 and Rapoport (1997) *Cephalalgia* 17: 464–465).

However, a significant portion of migraine patients remain who either require narcotic analgesic treatment or who may have significant disability despite the use of non-narcotic analgesia. A large number of patients go to hospital emergency rooms for acute treatment of prolonged migraine headache (Klapper et al. (1991) 31:523–524). Many of those patients may have used an ergotamine or triptan so that use of DHE, injectable sumatriptan or other related compounds would be contraindicated. Also, cardiovascular risk factors limit the safety of triptan use or dihydroergotamine; the new DHE nasal spray (Migranal) carries the same warnings as the triptans. (Kelly (1995) *Neurology* 45:11–13; Maxalt:MSD, Ltd. (1998) Insert; and Physician's Desk Reference, 53 Edition, Medical Economics Comp. (1999) pp 2061). Finally, a number of patients presenting to the emergency room have associated analgesic rebound headache, with or without chronic daily headache, in which cases further analgesic use is problematic (Silberstein and Young (1995) *Drug Saf.* 13:133–144).

SUMMARY OF THE INVENTION

This invention is based on the discovery of an effective acute treatment for migraines which involves intravenous injection of valproate sodium, also referred to herein according to its tradename, Depacon™. In particular, it has been discovered that intravenous valproate is an alternative therapy for abortive treatment of moderate to severe prolonged acute migraine headache.

DETAILED DESCRIPTION AND EXEMPLIFICATION

The present invention describes the results of studies using intravenous valproate ("VPA") for abortive treatment of acute migraine headache. The present studies were designed, in particular, to determine the possible effectiveness of intravenous administration of VPA for the treatment of acute migraine headache of significant duration. Accordingly, the invention provides methods of treating acute migraine headache in an subject in need of treatment. In one embodiment, the method involves administering to the subject an effective dose of intravenous valproate. Administration of intravenous valproate is preferably such that the severity and/or duration of acute migraine headache is lessened or reduced. Alternatively, administration is such that a symptom selected from the group consisting of nausea, photophobia, and phonophobia is lessened or reduced. In a preferred embodiment, about 100 mg to 2000 mg valproate are administered to a subject. Preferably about 200 mg to 1500 mg are administered, more preferably about 300 mg to 1000 mg are administered, and even more preferably about 250 mg to 750 mg of valproate are administered. In a particularly preferred embodiment, about 500 mg valproate are administered to the subject. In another embodiment, the valproate administered to the subject is administered over 1 hour. In yet another embodiment, the valproate is administered to a subject over 30 minutes. In yet another embodiment, the valproate is administered to a subject over 30 minutes to 1 hour. In yet another embodiment, the valproate is administered to a subject over 15 minutes to 30 minutes. In yet another embodiment, the valproate is administered to a subject over 5 minutes to 15 minutes. In yet another embodiment, the valproate is administered to a subject over 1 minute to 5 minutes. In yet another embodiment, the valproate is administered to the subject in more than one dose.

The invention is illustrated, in essence, by the following examples which should not be construed as limiting. The contents of all references cited throughout this application are hereby incorporated by reference.

EXAMPLE 1

Pilot Study

This Example describes the results of a pilot study using intravenous valproate for abortive treatment of acute migraine headache.

Methods. Patients with established diagnosis of migraine with and without aura were considered for randomization to intravenous ("IV") valproate ("VPA") or intramuscular ("IM") dihydroergotamine ("DHE") with metoclopramide, also referred to herein as Reglan®, for patients with moderate to severe migraine headaches of duration of 24 to 96 hrs. Patients received intravenous infusion of 500 mgs of valproate over 30 mins or 1 mg DHE with 10 mgs metoclopramide IM. Headache severity, presence of nausea, phonophobia and photophobia were rated at baseline, 1 hr, 2 hrs, and 4 hrs. Table I and II. There were 5 patients in each group.

Results. Of the 5 patients receiving valproate, 4 of the 5 had response of their headaches from moderate or severe to none or mild at 1 hr, 2 hrs, and 4 hrs. Of the 5 patients receiving DHE, 3 of the 5 patients had headache response to moderate or severe to mild or none at 1 hr, 2 hrs, and 4 hrs. Table III. Of patients receiving valproate, 4 of 5 had nausea at baseline, 1 had nausea at 1 and 2 hrs, and all had relief of nausea at 4 hrs. In the DHE group, 2 of 5 had nausea at baseline, and 1 had nausea at 1 hr, 2 hrs, and 4 hrs. Table IVa. In the valproate group, all had photophobia at baseline, 4 of 5 had relief of photophobia at 1 hr and 2 hrs, and all had relief at 4 hrs. In the DHE group, 3 of 5 had relief of photophobia at 1 hr, 4 of 5 had relief at 2 hrs and 4 hrs. In the valproate group, 4 of 5 had relief of phonophobia at 1 hr, 2 hrs, and all had relief at 4 hrs. In the DHE group, 2 of 5 had relief of phonophobia at 1 hr, and 3 of 5 had relief of phonophobia at 2 hrs and 4 hrs. Table IVb.

Conclusions. Intravenous valproate is an alternative therapy for abortive treatment of moderate to severe prolonged acute migraine headache. Anti-convulsant mechanisms may be relevant to treatment of headache symptomatology.

TABLE I

DEPACON IV 500 MG

| Patient | | 0-h | 1-h | 2-h | 4-h | 24-h |
|---|---|---|---|---|---|---|
| JV | Headache Severity | 3 | 0 | 0 | 0 | 0 |
|  | Nausea/vomiting | + | 0 | 0 | 0 | 0 |
|  | Photophobia | + | 0 | 0 | 0 | 0 |
|  | Phonophobia | + | 0 | 0 | 0 | 0 |
| KJ | Headache Severity | 3 | 1 | 1 | 0 | 1 |
|  | Nausea/vomiting | + | 0 | 0 | 0 | 0 |
|  | Photophobia | + | + | + | 0 | 0 |
|  | Phonophobia | + | + | + | 0 | 0 |
| LF | Headache Severity | 2 | 1 | 1 | 1 | 2 |
|  | Nausea/vomiting | 0 | 0 | 0 | 0 | 0 |
|  | Photophobia | + | 0 | 0 | 0 | + |
|  | Phonophobia | + | 0 | 0 | 0 | + |
| PD | Headache Severity | 2 | 0 | 1 | 2 | 2 |
|  | Nausea/vomiting | + | 0 | 0 | 0 | + |
|  | Photophobia | + | 0 | 0 | 0 | 0 |
|  | Phonophobia | 0 | 0 | 0 | 0 | 0 |
| CH | Headache Severity | 3 | 2 | 1 | 0 | 3 |
|  | Nausea/vomiting | + | + | + | 0 | + |
|  | Photophobia | + | 0 | 0 | 0 | + |
|  | Phonophobia | + | 0 | 0 | 0 | + |

TABLE II

DHE 1 mg Reglan 10 mg

| Patient | | 0-h | 1-h | 2-h | 4-h | 24-h |
|---|---|---|---|---|---|---|
| DW | Headache Severity | 3 | 2 | 2 | 2 | |
|  | Nausea/vomiting | + | 0 | + | + | |
|  | Photophobia | + | + | + | + | |
|  | Phonophobia | + | 0 | + | + | |

TABLE II-continued

DHE 1 mg Reglan 10 mg

| Patient | | 0-h | 1-h | 2-h | 4-h | 24-h |
|---|---|---|---|---|---|---|
| EM | Headache Severity | 2 | 3 | 3 | 3 | 1 |
|  | Nausea/vomiting | 0 | 0 | 0 | 0 | 0 |
|  | Photophobia | + | + | + | + | 0 |
|  | Phonophobia | 0 | + | + | + | 0 |
| JB | Headache Severity | 3 | 0 | 0 | 1 | 1 |
|  | Nausea/vomiting | 0 | 0 | 0 | 0 | 0 |
|  | Photophobia | + | 0 | 0 | 0 | 0 |
|  | Phonophobia | + | 0 | 0 | 0 | 0 |
| AK | Headache Severity | 3 | 1 | N/D | 0 | 0 |
|  | Nausea/vomiting | 0 | 0 | N/D | 0 | 0 |
|  | Photophobia | + | + | N/D | 0 | 0 |
|  | Phonophobia | + | + | N/D | 0 | 0 |
| CH | Headache Severity | 3 | 0 | 0 | 0 | 2 |
|  | Nausea/vomiting | + | + | + | + | + |
|  | Photophobia | + | 0 | 0 | 0 | + |
|  | Phonophobia | + | 0 | 0 | 0 | 0 |

TABLE III

% Headache Relief

|  | 1-h | 2-h | 4-h | 24-h |
|---|---|---|---|---|
| Depacon | 60 | 100 | 80 | 40 |
| DHE/Reglan | 60 | 50 | 60 | |

TABLE IVa

% Improvement of Migraine-associated Symptoms

| % experiencing nausea | Depacon | DHE |
|---|---|---|
| 0-h | 80 | 40 |
| 1-h | 20 | 20 |
| 2-h | 20 | 50 |
| 4-h | 0 | 40 |
| 24-h | 40 | |

TABLE IVb

|  | Depacon | DHE |
|---|---|---|
| % experiencing photophobia | | |
| 0-h | 100 | 100 |
| 1-h | 20 | 60 |
| 2-h | 20 | 50 |
| 4-h | 0 | 40 |
| 24-h | 40 | |
| % experiencing phonphobia | | |
| 0-h | 80 | 80 |
| 1-h | 20 | 40 |
| 2-h | 20 | 50 |
| 4-h | 0 | 40 |
| 24-h | 40 | |

EXAMPLE 2

Expanded Study

This Example describes an expanded study and analysis of the effectiveness of intravenous VPA for the treatment of acute migraine headache of significant duration. Patient data from the pilot study described in Example 1 has been incorporated and further analyzed in addition to new patient data.

Design. Twenty patients with moderate to severe headaches of 24–72 hours duration were seen at the Western New England Headache Clinic. Patients alternately received intravenous VPA 500 mgs over 15–30 minutes, or dihydroergotamine ("DHE") 1 mg with metoclopramide 10 mgs intramuscularly ("IM"). Age ranged from 22 to 73 years. Patients rated severity of headache, presence or absence of nausea, photophobia, and phonophobia at 1, 2 and 4 hrs. Table V and Table VI.

Results. In the 10 patients receiving DHE and metoclopramide, 40% had headache relief at 1 hour, 50% at 2 hours, 60% at 4 hours. The percent with nausea at 0, 1, 2, and 4 hours was 60%, 10%, 20%, 30% respectively, photophobia at 0, 1, 2, and 4 hours 100%, 50%, 50%, 40% respectively, phonophobia at 0, 1, 2, and 4 hours 80%, 30%, 50%, 40% respectively. In the 10 patients receiving i.v. VPA, 60% had headache relief at 1 hour, 70% at 2 hours, 70% at 4 hours, the percent with nausea at 0, 1, 2, and 4 hours was 70%, 30% 30%, 20% respectively, photophobia at 0, 1, 2, and 4 hours was 100%, 40%, 40%, 30% respectively, and phonophobia at 0, 1, 2, and 4 hours was 90%, 40%, 40%, 30% respectively. Table VII.

Conclusions. The results of the present study indicate that intravenous VPA is at least as efficacious as DHE for abortive treatment of acute migraine. Accordingly, intravenous VPA offers a treatment option for migraine headache patients who have recently used a triptan or DHE without the risk of drug-drug interaction or cardiovascular complications.

TABLE V

| | | DHE 1 mg IM Reglan 10 mg IM | | | | | |
|---|---|---|---|---|---|---|---|
| Patient | Headache Duration | | 0-h | 1-h | 2-h | 4-h | 24-h |
| DW | 24 hours | Headache Severity | 3 | 2 | 2 | 2 | 0 |
| | | Nausea/vomiting | – | 0 | – | – | 0 |
| | | Photophobia | – | – | – | – | 0 |
| | | Phonophobia | – | 0 | – | – | 0 |
| EM | 36 hours | Headache Severity | 2 | 3 | 3 | 3 | 1 |
| | | Nausea/vomiting | 0 | 0 | 0 | 0 | 0 |
| | | Photophobia | – | – | – | – | 0 |
| | | Phonophobia | 0 | – | – | – | 0 |
| JB | 24 hours | Headache Severity | 3 | 0 | 0 | 1 | 1 |
| | | Nausea/vomiting | 0 | 0 | 0 | 0 | 0 |
| | | Photophobia | – | 0 | 0 | 0 | 0 |
| | | Phonophobia | – | 0 | 0 | 0 | 0 |
| CH | 72 hours | Headache Severity | 3 | 0 | 0 | 0 | 2 |
| | | Nausea/vomiting | – | – | – | – | – |
| | | Photophobia | – | 0 | 0 | 0 | – |
| | | Phonophobia | – | 0 | 0 | 0 | 0 |
| LH | 72 hours | Headache Severity | 3 | 3 | 2 | 0 | 0 |
| | | Nausea/vomiting | 0 | 0 | 0 | 0 | 0 |
| | | Photophobia | + | – | + | 0 | 0 |
| | | Phonophobia | + | + | + | 0 | 0 |
| GL | 48 hours | Headache Severity | 3 | 2 | 2 | 2 | 1 |
| | | Nausea/vomiting | + | 0 | 0 | 0 | 0 |
| | | Photophobia | + | + | + | + | 0 |
| | | Phonophobia | – | – | – | – | 0 |

TABLE V-continued

| | | DHE 1 mg IM Reglan 10 mg IM | | | | | |
|---|---|---|---|---|---|---|---|
| Patient | Headache Duration | | 0-h | 1-h | 2-h | 4-h | 24-h |
| CR | 72 hours | Headache Severity | 3 | 0 | 0 | 0 | 1 |
| | | Nausea/vomiting | + | 0 | 0 | 0 | 0 |
| | | Photophobia | + | 0 | 0 | 0 | 0 |
| | | Phonophobia | – | 0 | 0 | 0 | 0 |
| MM | 72 hours | Headache Severity | 2 | 0 | 0 | 0 | 0 |
| | | Nausea/vomiting | + | 0 | 0 | 0 | 0 |
| | | Photophobia | + | 0 | 0 | 0 | 0 |
| | | Phonophobia | + | 0 | 0 | 0 | 0 |
| JC | 24 hours | Headache Severity | 2 | 2 | 3 | 3 | 1 |
| | | Nausea/vomiting | 0 | 0 | – | – | 0 |
| | | Photophobia | – | – | – | – | 0 |
| | | Phonophobia | 0 | 0 | – | – | 0 |
| MJ | 48 hours | Headache Severity | 2 | 2 | 1 | 1 | 1 |
| | | Nausea/vomiting | + | 0 | 0 | 0 | 0 |
| | | Photophobia | + | 0 | 0 | 0 | + |
| | | Phonophobia | – | 0 | 0 | 0 | – |

TABLE VI

| | | Depacon IV 500 mg | | | | | |
|---|---|---|---|---|---|---|---|
| Patient | Headache Duration | | 0-h | 1-h | 2-h | 4-h | 24-h |
| JV | 24 hours | Headache Severity | 3 | 0 | 0 | 0 | 0 |
| | | Nausea/vomiting | – | 0 | 0 | 0 | 0 |
| | | Photophobia | – | 0 | 0 | 0 | 0 |
| | | Phonophobia | – | 0 | 0 | 0 | 0 |
| KJ | 48 hours | Headache Severity | 3 | 1 | 1 | 0 | 1 |
| | | Nausea/vomiting | – | 0 | 0 | 0 | 0 |
| | | Photophobia | – | – | – | 0 | 0 |
| | | Phonophobia | – | – | – | 0 | 0 |
| LF | 48 hours | Headache Severity | 2 | 1 | 1 | 1 | 2 |
| | | Nausea/vomiting | 0 | 0 | 0 | 0 | 0 |
| | | Photophobia | – | 0 | 0 | 0 | + |
| | | Phonophobia | – | 0 | 0 | 0 | – |
| PD | 48 hours | Headache Severity | 2 | 0 | 1 | 2 | 2 |
| | | Nausea/vomiting | – | 0 | 0 | 0 | + |
| | | Photophobia | – | 0 | 0 | 0 | 0 |
| | | Phonophobia | 0 | 0 | 0 | 0 | 0 |
| CH | 24 hours | Headache Severity | 3 | 2 | 1 | 0 | 3 |
| | | Nausea/vomiting | – | – | – | 0 | – |
| | | Photophobia | + | 0 | 0 | 0 | – |
| | | Phonophobia | + | 0 | 0 | 0 | + |
| BL | 72 hours | Headache Severity | 2 | 1 | 1 | 1 | 2 |
| | | Nausea/vomiting | + | 0 | 0 | 0 | 0 |
| | | Photophobia | + | + | + | + | + |
| | | Phonophobia | + | + | + | + | + |
| MMC | 48 hours | Headache Severity | 3 | 3 | 2 | 2 | 1 |
| | | Nausea/vomiting | + | – | – | + | + |
| | | Photophobia | + | + | + | + | + |
| | | Phonophobia | + | + | + | + | + |
| MC | 24 hours | Headache Severity | 2 | 2 | 2 | 1 | 0 |
| | | Nausea/vomiting | 0 | 0 | 0 | 0 | 0 |
| | | Photophobia | – | 0 | 0 | 0 | 0 |
| | | Phonophobia | – | 0 | 0 | 0 | 0 |
| MJ | 48 hours | Headache Severity | 2 | 1 | 1 | 1 | 1 |
| | | Nausea/vomiting | 0 | 0 | 0 | 0 | 0 |
| | | Photophobia | + | 0 | 0 | 0 | + |
| | | Phonophobia | + | 0 | 0 | 0 | + |
| LH | 48 hours | Headache Severity | 3 | 3 | 2 | 3 | 2 |
| | | Nausea/vomiting | + | – | – | + | + |
| | | Photophobia | – | – | – | – | + |
| | | Phonophobia | – | – | – | – | – |

TABLE VII

ANALYSIS

% Headache Relief

|  | 1-h | 2-h | 4-h | 24-h |
|---|---|---|---|---|
| Depacon | 60 | 70 | 70 | 50 |
| DHE | 40 | 50 | 60 | 90 |

% Improvement of Migraine-associated Symptoms

|  | Depacon | DHE |
|---|---|---|
| % experiencing Nausea | | |
| 0-h | 70 | 60 |
| 1-h | 30 | 10 |
| 2-h | 30 | 20 |
| 4-h | 20 | 30 |
| 24-h | 40 | 10 |
| % experiencing Photophobia | | |
| 0-h | 100 | 100 |
| 1-h | 40 | 50 |
| 2-h | 40 | 50 |
| 4-h | 30 | 40 |
| 24-h | 60 | 20 |
| % experiencing Phonophobia | | |
| 0-h | 90 | 80 |
| 1-h | 40 | 30 |
| 2-h | 40 | 50 |
| 4-h | 30 | 40 |
| 24-h | 60 | 10 |

EXAMPLE 3

Further Expanded Study

This Example describes a further expanded study and analysis of the effectiveness of intravenous VPA for the treatment of acute migraine headache of significant duration. Patient data from the study described in Examples 1 and 2 have been incorporated and further analyzed in addition to new patient data.

Design and Methods. Participants (N=40) were from age 14 to 74 and were established patients of the Western New England Headache Clinic. Patients called to report the pressure of prolonged moderate to severe migraine. They had no evidence of conditions other than migraine to cause headache and were medically stable. None of the patients had a known allergy to Depacon™ or DHE; none was pregnant. Patients received a neurological and general physical examination and filled out a four grade baseline headache rating from developed by Western New England Headache Clinic (see Table 2). The patients then received either 500 mg Depacon™ over 15–30 minutes administered in 100 ccs D5W, or 1 mg DHE intramuscularly preceded by 10 mg metoclopramide intramuscularly. Headache severity and associated symptomatology were rated 1, 2, and 4 hours.

Results.

A total of 40 patients were randomized, 20 in the Depacon™ group and 20 in the DHE group. Table VII summarizes the number of patients in each group by severity of headache (moderate or severe), demographic data and medication assignment.

Table VIII shows respond rate and headache severity for baseline, 1, 2 and 4 hours.

Table IX shows the associated symptomatology experienced at baseline, 1, 2 and 4 hours. The majority of patients had meaningful response in both groups, but the Depacon™ group responded somewhat better, although not statistically significantly ($P>0.05$).

Table X shows the numbers and percentages of symptom free patients at 1, 2 and 4 hours.

TABLE VII

Baseline Patient Characteristics

|  | DHE (N = 20) | Depacon ® (N = 20) |
|---|---|---|
| Gender | | |
| Female | 18 (90%) | 17 (85%) |
| Male | 2 (10%) | 3 (15%) |
| Age in Years | | |
| Mean (Range) | 43.0 (14–71) | 41.0 (14–73) |
| Duration of Headache | | |
| Mean (Range) in Hours | 49.2 (24–96) | 46.4 (24–75) |
| Severity of Headache | | |
| Moderate | 8 (40%) | 6 (30%) |
| Severe | 12 (60%) | 14 (70%) |

TABLE VII

Responder Rate and Headache Severity*

|  | Baseline | 1 hour | 2 hours | 4 hours |
|---|---|---|---|---|
| Depacon | 2.7 | 1.8 (50%) | 1.5 (60%) | 1.4 (60%) |
| DHE | 2.6 | 1.5 (45%) | 1.4 (50%) | 1.2 (60%) |

TABLE IX

Associated Symptomatology

|  | Baseline | 1 hour | 2 hours | 4 hours |
|---|---|---|---|---|
| Number (or %) of Patients Who Reported Nausea | | | | |
| Depacon ® | 15 (75%) | 8 (53%) | 8 (53%) | 7 (47%) |
| DHE 12 | (60%) | 5 (42%) | 6 (50%) | 6 (50%) |
| Number (or %) of Patients Who Reported Photophobia | | | | |
| Depacon ® | 20 (100%) | 14 (70%) | 10 (50%) | 9 (45%) |
| DHE 12 | 20 (100%) | 15 (75%) | 13 (65%) | 11 (55%) |
| Number (or %) of Patients Who Reported Phonophobia | | | | |
| Depacon ® | 19 (95%) | 14 (74%) | 11 (58%) | 10 (53%) |
| DHE 12 | 18 (90%) | 12 (67%) | 12 (67%) | 11 (61%) |

TABLE X

Symptom Free Patients in Each Group at 4 hours (no headache or associated symptomatology)

|  | Symptom Free at 1 hour | Symptom Free at 2 hours | Symptom Free at 4 hours |
|---|---|---|---|
| Depacon ® (N = 20) | 2 (10%) | 3 (15%) | 5 (25%) |
| DHE (N = 20) | 3 (15%) | 5 (25%) | 6 (30%) |

Analysis. This study demonstrates that Depacon™ is an effective symptomatic treatment for migraine headache and comparable in efficacy to DHE. Depacon™ appears to act as an abortive migraine medication, possibly by a GABAergic mechanism. (Cutrer et al. (1997) *Cephalalgia* 17:93–100). Headache associated symptomatology responded equally well and comparably to the combination of DHE and metoclopramide. The cohort treated with Depacon™ was remarkably free of adverse event; all were independent and returned to home after receiving treatment. This is especially remarkable in view of the fact that headache, nausea and vomiting are listed among the adverse side effects associated with both divalproex sodium (Depakote™) and intravenous valproate (Depacon™) treatments.

Depacon™ is FDA approved for treatment of epilepsy and has a favorable safety profile. We had no adverse events in any of the 20 patients receiving 500 mg Depacon™ given during 15 to 30 minutes infusion. In the typical migraineur who presents in a clinic or emergency room, Depacon™ could be used advantageously among those who have recently used an ergotamine or triptan, since there is no significant drug-drug interaction between Depacon™, ergotamine or triptan.

Divalproex sodium tablets (Depakote™) have been reported to be useful for preventative treatment of migraine headaches with or without aura, with several studies showing efficacy (Jensen et al. (1995) *Arch* Neurol. 52:281–286 and Hering and Kuritzky (1992) *Cephalalgia* 12:81–84). The FDA has approved Depakote™ for prevention of migraine headaches. However, the studies described herein (e.g., Examples 1–2) represent the first demonstration of the use of intravenous valproate, Depacon™, for abortive treatment of acute migraine headaches. This novel therapy offers a treatment option with little risk of drug-drug interaction or cardiovascular complications for migraine patients who have recently used an ergotomine or triptan.

In these pilot studies, Depacon™ is determined to be at least comparable to the traditional combination of DHE and metoclopramide in headache relief and associated symptomatologies. Although the DHE and metoclopramide were administered intramuscularly in this study, it is unlikely this method of administration affected the degree of relief, or time of action, for these patients compared to intravenous DHE and metoclopramide administration.

Conclusion. Depacon™ is equal to and in some respects superior to dihydroergotamine therapy for abortive treatment of prolonged moderate to severe acute migraine headache. Depacon™ offers an effective therapy option when patients' egotamine or triptan use presents the possibility of adverse drug interactions or cardiovascular effects that may be consequent to dihydroergotamine therapy (e.g., patients who have had use of ergotamine or triptan within 24 hours prior to clinic or emergency room arrival). Depacon™ would not be associated with analgesic rebound, or patients' inappropriate medication-seeking that the use of narcotic analgesics can promote.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of treating acute migraine headache in an subject comprising administering to the subject an effective dose of intravenous valproate such that acute migraine headache is lessened or reduced in said subject, wherein about 250 mg to 750 mg of valproate is administered to a subject over 30 minutes to 1 hour.

2. A method of treating acute migraine headache in an subject comprising administering to the subject an effective dose of intravenous valproate such that acute migraine headache is lessened or reduced in said subject, wherein about 250 mg to 750 mg of valproate is administered to a subject over 15 minutes to 30 minutes.

3. A method of treating acute migraine headache in an subject comprising administering to the subject an effective dose of intravenous valproate such that acute migraine headache is lessened or reduced in said subject, wherein about 250 mg to 750 mg of valproate is administered to a subject over 5 minutes to 15 minutes.

4. A method of treating acute migraine headache in an subject comprising administering to the subject an effective dose of intravenous valproate such that acute migraine headache is lessened or reduced in said subject, wherein about 250 mg to 750 mg of valproate is administered to a subject over 1 minute to 5 minutes.

5. The method of any one of claims 1–4, wherein about 500 mg valproate is administered to the subject.

6. The method of any one of claims 1–4, wherein administration is such that severity of acute migraine headache is lessened or reduced.

7. A method of any one of claims 1–4, wherein administration is such that duration of acute migraine headache is lessened or reduced.

8. The method of any one of claims 1–4, wherein administration is such that a symptom selected from the group consisting of nausea, photophobia, and phonophobia is lessened or reduced.

9. The method of any one of claims 1–4, wherein the valproate is administered to the subject in more than one dose.

* * * * *